(12) United States Patent
Divo et al.

(10) Patent No.: US 6,786,894 B2
(45) Date of Patent: Sep. 7, 2004

(54) ABSORBENT ARTICLE HAVING LIQUID HANDLING MEMBER WHICH COLLAPSES UNDER HIGH PRESSURES

(75) Inventors: Michael Divo, Friedrichsdorf (DE); Peter Dziezok, Hochheim (DE); John Peter Lankhof, Bad Homburg (DE)

(73) Assignee: The Procter & Gamble Company, Cincinnati, OH (US)

( * ) Notice: Subject to any disclaimer, the term of this patent is extended or adjusted under 35 U.S.C. 154(b) by 24 days.

(21) Appl. No.: 10/148,359

(22) PCT Filed: Nov. 29, 2000

(86) PCT No.: PCT/US00/32548
§ 371 (c)(1),
(2), (4) Date: May 29, 2002

(87) PCT Pub. No.: WO01/37772
PCT Pub. Date: May 31, 2001

(65) Prior Publication Data
US 2002/0183705 A1 Dec. 5, 2002

(30) Foreign Application Priority Data

| Nov. 29, 1999 | (EP) | 99123656 |
|---|---|---|
| Dec. 10, 1999 | (EP) | 99124637 |
| Apr. 4, 2000 | (EP) | 00107272 |

(51) Int. Cl.$^7$ ............................................ A61F 13/15
(52) U.S. Cl. .................. 604/385.101; 604/378; 604/369; 604/379; 604/383; 604/385.01
(58) Field of Search .................. 604/385.01, 378, 604/385.101, 369, 379, 383; 428/131–140, 170–172

(56) References Cited
U.S. PATENT DOCUMENTS

| 3,860,003 A | 1/1975 | Buell |
|---|---|---|
| 3,870,767 A | 3/1975 | Grimaud et al. |
| 3,911,173 A | 10/1975 | Sprague, Jr. |
| 4,573,986 A | 3/1986 | Minetola et al. |
| 4,610,678 A | 9/1986 | Weisman et al. |
| 4,673,402 A | 6/1987 | Weisman et al. |
| 4,785,996 A | 11/1988 | Ziecker et al. |
| 4,834,735 A | 5/1989 | Alemany et al. |
| 4,842,666 A | 6/1989 | Werenicz |
| 4,888,231 A | 12/1989 | Angstadt |
| 5,151,092 A | 9/1992 | Buell et al. |
| 5,221,274 A | 6/1993 | Buell et al. |
| 5,554,143 A | 9/1996 | Roe et al. |
| 5,554,144 A | 9/1996 | Roe et al. |
| 5,554,145 A | 9/1996 | Roe et al. |
| 5,556,394 A | 9/1996 | Roe et al. |
| 5,569,232 A | 10/1996 | Roe et al. |

FOREIGN PATENT DOCUMENTS

| EP | 0 951 913 A1 | 10/1999 |
|---|---|---|
| EP | 0 985 740 A1 | 3/2000 |
| EP | 0 985 741 A1 | 3/2000 |
| EP | 1 051 960 A1 | 11/2000 |
| WO | WO 95/05139 A1 | 2/1995 |
| WO | WO 96/00548 A1 | 1/1996 |
| WO | WO 96/16682 A1 | 6/1996 |
| WO | WO 97/42356 A1 | 11/1997 |
| WO | WO 99/25293 A1 | 5/1999 |
| WO | WO 99/25294 A1 | 5/1999 |
| WO | WO 01/37772 A1 | 5/2001 |

*Primary Examiner*—John J. Calvert
*Assistant Examiner*—Jacqueline Stephens
(74) *Attorney, Agent, or Firm*—Edward J. Milbrada; Eileen L. Hughett; Ken K. Patel (57) ABSTRACT

The present invention relates to absorbent articles for retaining body fluids such as urine, menses, or fecal material. In particular, the absorbent article of the present invention comprises a liquid handling member that collapses at a pressure between 2756 Pascal (0.4 psi) and 3447 (0.5 psi) in order to reduce the likelihood of causing skin marking.

6 Claims, 1 Drawing Sheet

FIG.1

ABSORBENT ARTICLE HAVING LIQUID HANDLING MEMBER WHICH COLLAPSES UNDER HIGH PRESSURES

FIELD OF THE INVENTION

The present invention relates to absorbent articles for retaining body fluids such as urine, menses, or fecal material, and in particular to their ability to acquire and retain aqueous based materials. The invention further relates to disposable absorbent articles such as baby diapers or training pants, adult incontinence products, and feminine hygiene products.

BACKGROUND

Disposable absorbent articles such as diapers, sanitary napkins, adult incontinence products, and the like are well known in the art. Such articles are used for handling body exudates such as urine, menses, fecal material, and other aqueous body liquids.

It has been a recent trend to provide absorbent articles which comprise liquid handling members of a low density. Such liquid handling members are capable of rapidly acquiring large volumes of body exudates deposited onto the absorbent article. In particular for the handling of high viscosity liquids, it is desired that the liquid handling members have large open pores. For example such structures are described in WO 95/05139 (Roe), in WO 99/25293 (Bast et al.), and in WO 99/25294 (Roe et al.).

On the other hand, liquid handling members having large open pores generally do not have planar major surfaces since at least some of the large open pores will extend to the surfaces. During use of and article comprising such a liquid handling member, the pressure exerted onto the article for example by the wearer sitting on the article has to be carried by the remaining parts of the surface. Hence, a relatively high pressure is exerted onto the skin of the wearer at these surface parts leading to a undesirably low level of wearing comfort and ultimately to skin marking.

Hence, it is an object of the present invention to provide a disposable absorbent article which overcomes the problems posed by the prior art absorbent articles.

It is a further object of the present invention to provide a disposable absorbent article comprising a liquid handling member that collapses at a pressure between 2756 Pascal (0.4 psi) and 3447(0.5 psi).

SUMMARY OF THE INVENTION

The present invention provides an disposable absorbent article comprising a liquid pervious structured carrier, a liquid impervious backsheet at least partially peripherally joined to the structured carrier, a liquid storage structure positioned intermediate the topsheet and the backsheet, and a liquid handling structure positioned intermediate the topsheet and the liquid storage structure, the liquid handling structure having a caliper under a confining pressure of 689 Pascal (0.1 psi) of at least 0.5 mm. The absorbent article of the present invention is characterized in that the liquid handling structure has a caliper under a confining pressure of 2756 Pascal (0.4 psi) of at least 80% of the caliper under a confining pressure of 689 Pascal and the liquid handling structure has a caliper under a confining pressure of 3447 Pascal (0.5 psi) of less than 80% of the caliper under a confining pressure of 689 Pascal.

DETAILED DESCRIPTION OF THE INVENTION

The absorbent article of the present invention is described in the following by means of a variety of different embodiments and by means of a variety of is different features. Further embodiments of the present invention may be obtained by combining features of one embodiment with features of another embodiment disclosed herein and/or with other features disclosed herein. These further embodiments are considered to be implicitly disclosed herein and hence form part of the present invention. It will be apparent to the skilled person that combinations of certain features may lead to non-functional articles not forming part of the present invention.

Absorbent Article

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and adult incontinent persons and is worn about the lower torso of the wearer. The present invention is also applicable to other absorbent articles such as incontinence briefs, incontinence undergarments, absorbent inserts, diapers holders and liners, feminine hygiene garments, and the like.

Diaper

Figure 1:
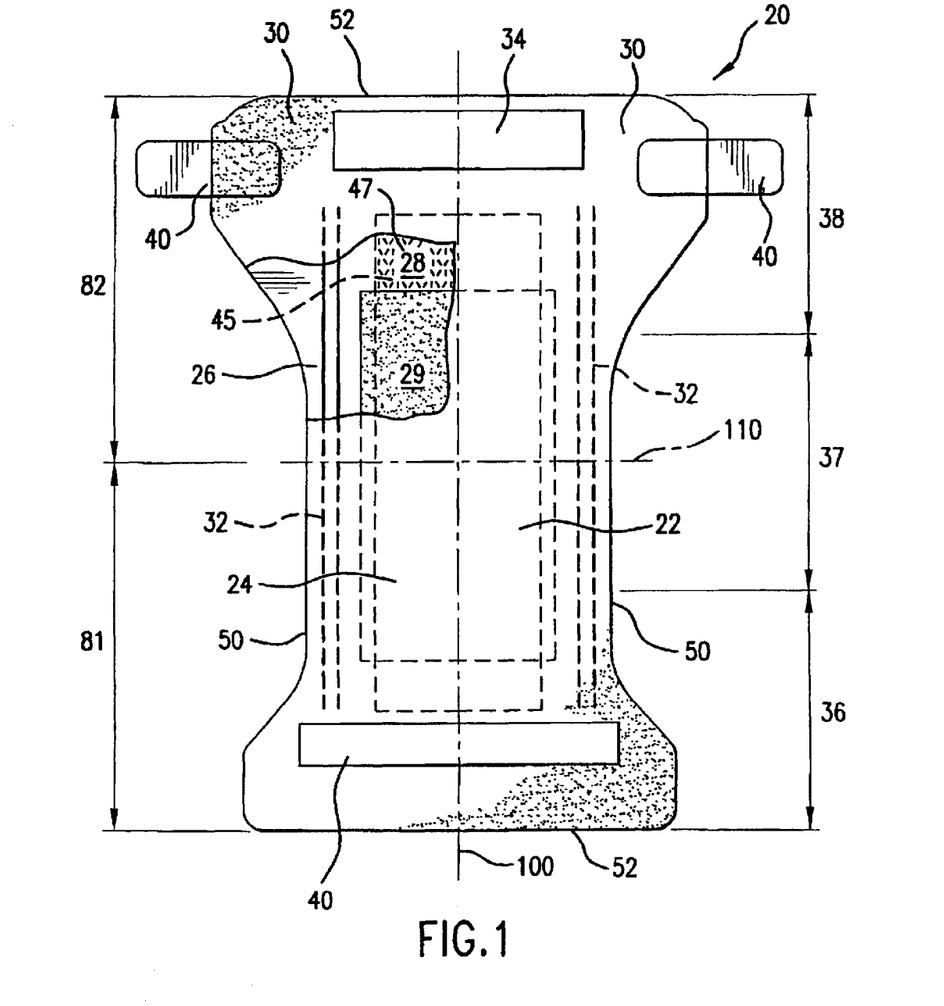
FIG. 1 is a plan view of an absorbent article embodiment of the present invention having portions cut away to reveal the underlying structure, the garment-facing surface of the diaper facing the viewer.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious structured carrier 24; a liquid impervious backsheet 26; an liquid storage structure 28, which is preferably positioned between at least a portion of the structured carrier 24 and the backsheet 26; a liquid handling structure 29 positioned between the structured carrier 24 and the liquid storage structure 28; side panels 30; elasticized leg cuffs 32; an elastic waist feature 34; and a fastening system generally designated 40.

Diaper 20 is shown in FIG. 1 to have a front waist region 36, a rear waist region 38 opposed to the front waist region 36 and a crotch region 37 located between the front waist region and the rear waist region. The diaper 20 further has a first region 81 juxtaposed with the front of the wearer while the diaper 20 is being worn and a second region 82 opposed to the first region 81 and juxtaposed with the back of the wearer while the diaper 20 is being worn. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20. In FIG. 1 the first region 31 is shown as extending from one end edge 35 to the lateral centerline 21 and the second region 32 is shown as extending from the opposing end edge 35 to the lateral centerline 21. For purposes of discussion, the lateral centerline 21 is shown as the boundary between the first region 31 and the second region 32 in FIG. 1. However, the boundary between the first region 31 and the second region 32 may be positioned at other locations, for example closer to one of the respective end edges 52. The first region 31 being juxtaposed with the front of the wearer may be superior in the handling of urine. The second region being juxtaposed with the back of the wearer may be superior in the handling of fecal material, in particular low-viscosity fecal material.

The chassis 22 of the diaper 20 comprises the main body of the diaper 20. The chassis 22 comprises at least a portion of the liquid storage structure 28 and preferably an outer covering layer including the structured carrier 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a structured carrier, a backsheet, and an liquid storage structure. In such cases, the holder and/or the liner may include a fastening element which is used to hold the liner in place throughout the time of use.) For unitary absorbent articles, the chassis 22 comprises the main structure of the diaper with other features added to form the composite diaper structure.

FIG. 1 shows an embodiment of the diaper 20 in which the structured carrier 24 and the backsheet 26 have length and width dimensions generally larger than those of the liquid storage structure 28 and the liquid handling structure 29. The structured carrier 24 and the backsheet 26 extend beyond the edges of the liquid storage structure 28 to thereby form the periphery of the diaper 20.

While the structured carrier 24, the backsheet 26, and the chassis 22 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993. is Other suitable diaper chassis design are disclosed in U.S. Pat. No. 5,569,232 entitled "Absorbent Article With Multiple Zone Structural Elastic-Like Film Web Extensible Waist Feature" which issued to Roe et al. on Oct. 29, 1996; U.S. Pat. No. 5,554,144 entitled "Absorbent Article With Multiple Zone Structural Elastic-Like Film Web Extensible Waist Feature" which issued to Roe et al. on Sep. 10, 1996; U.S. Pat. No. 5,554,143 entitled "Absorbent Article With Multiple Zone Structural Elastic-Like Film Web Extensible Waist Feature" which issued to Roe et al. on Sep. 10, 1996; U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,556,394 entitled "Absorbent Article With Multiple Zone Structural Elastic-Like Film Web Extensible Waist Feature" which issued to Roe et al. on Sep. 17, 1996. Each of these references is hereby incorporated by reference herein.

The inner surface of the diaper 20 comprises that portion of the diaper 20 which is adjacent to the wearer's body during use (i.e., the inner surface generally is formed by at least a portion of the structured carrier 24 and other components joined to the structured carrier 24). The outer surface comprises that portion of the diaper 20 which is positioned away from the wearer's body (i.e., the outer surface generally is formed by at least a portion of the backsheet 26 and other components joined to the backsheet 26) during use.

Aqueous Liquid Handling Performance

The liquid handling performance for aqueous liquids is a key feature of the present invention. The term "aqueous liquids" as used herein includes but is not limited to body exudates such as urine, fecal material, menses, blood, sweat.

Liquid Acquisition

The term "liquid acquisition" as used herein refers to the rate at which liquid which is deposited on top of the structured carrier of the present invention is absorbed from the surface of the structured carrier into the absorbent article.

The liquid acquisition performance of the absorbent article of the present invention is assessed via the Finished-Product-Acquisition Test.

The absorbent article of the present invention has a liquid acquisition rate of at least 3.75 ml/s in the first gush, preferably of at least 4 ml/s in the first gush, more preferably at least 4.5 ml/s in the first gush, and most preferably at least 5 ml/s in the first gush. The absorbent article of the present invention further has a liquid acquisition rate of at least 0.5 ml/s in the fourth gush, preferably at least 0.6 ml/s in the fourth gush, more preferably at least 0.8 ml/s in the fourth gush, and most preferably at least 1.0 ml/s in the fourth gush.

Liquid Rewet

The term "liquid rewet" as used herein refers to already acquired liquid that is subsequently squeezed out through the structured carrier of a loaded absorbent article under pressure.

The liquid rewet performance of the absorbent article of the present invention is assessed via the Collagen Rewet Test and is quantified by the Skin Hydration value.

The front region of the absorbent article of the present invention has a Skin Hydration value of less than 120 mg, preferably a Skin Hydration value of less than 90 mg, more preferably a Skin Hydration value of less than 70 mg, and most preferably a Skin Hydration value of less than 50 mg.

Optionally, the back region may have a Skin Hydration value of less than 120 mg, preferably a Skin Hydration value of less than 90 mg, more preferably a Skin Hydration value of less than 70 mg, and most preferably a Skin Hydration value of less than 50 mg.

Topsheet Wetness

In order to support the dry touch of the user facing surface of the absorbent article of the present invention, the absorbent article of the present invention preferably has a topsheet wetness of less than 300 mg, more preferably less than 200 mg, even more preferably less than 100 mg, even more preferably less than 50 mg, most preferably less than 25 mg according to the Topsheet-Finished-Product-Dryness Method.

High Viscosity Liquid Handling

In addition, the absorbent article of the present invention preferably provides high viscosity liquid handling, and in particular liquid handling of viscous fluid body waste.

As used herein, the term "viscous fluid bodily waste" or "VFBW" generally refers to any waste discarded from the body which has a viscosity of greater than about 10 cP and less than about $2 \times 10^5$ cP at a shear rate of one 1/sec, (at about 35 degrees C.), more particularly between about $10^3$ cP and $10^5$ cP at a one 1/sec shear rate, in a controlled stress rheometry test using parallel plates on a controlled stress rheometer. (For reference, water is at 1.0 cP at 20 degrees C. and Jif Creamy peanut butter (available from the Procter & Gamble Co., Cincinnati, Ohio) is approximately $4 \times 10^5$ cP at 25 degrees C. at this same shear rate).

Storage Under Pressure

Once viscous fluid bodily waste has penetrated the liquid handling structure, it is desirable to store or hold the waste away from the wearer during the remainder of the wearing cycle and away from the caregiver during the changing process. As used herein, the term "store" refers to the physical separation of material deposited in a diaper from the body-facing surface of the article such that the material deposited in the diaper is not immediately in contact with or accessible to the wearer's skin. Storage Under Pressure, or "storage," is measured as the amount of material held in the structure on a unit area basis, as described in the Test Method Section below. If the Storage Under Pressure capacity is too low, the absolute quantity of viscous fluid bodily waste that can be stored away from skin access per unit area of the structure will be reduced. Adequate storage capacity is essential to reduce the probability of leakage and the area of skin contaminated by viscous fluid bodily waste because viscous fluid bodily waste that has been stored is less likely to be available to the body-facing surface of the structure for leakage and migration within the article.

In preferred embodiments of the present invention the absorbent article should include a liquid handling structure having a Storage Under Pressure value greater than about 500 grams per square meter ($g/m^2$) of the liquid handling structure of viscous fluid bodily waste. More preferably, the liquid handling structure should have a Storage Under Pressure value greater than about 750 $g/m^2$ of viscous fluid bodily waste. Even more preferably, the liquid handling structure should have a Storage Under Pressure value greater than about 1000 $g/m^2$ of viscous fluid bodily waste, and most preferably greater than about 1100 $g/m^2$ of viscous fluid bodily waste. Generally, Storage Under Pressure values between at least about 500 $g/m^2$ and about 10000 $g/m^2$, and preferably between about 750 $g/m^2$ and about 10000 $g/m^2$ have been found to be acceptable. (These preferred Storage Under Pressure parameters relate to integrated articles which are preferably evaluated as they are intended for use. Accordingly, all of the components or layers of the article should be configured as they would be during normal use when the measurement of their performance is made.)

Retention and Immobilization Under Compressed Inversion

Viscous fluid bodily waste that is accepted by, or penetrates, the absorbent article is preferably also retained in the diaper away from the wearer. One preferred way to retain bodily waste, especially viscous fluid bodily waste, is to immobilize the waste in a location away from the wearer. As used herein, the term "immobilize" refers to the ability of the material or structure to retain stored viscous fluid bodily waste under an applied pressure and/or the influence of gravitational forces. Immobilization Under Compressed Inversion, or "immobilization," may be accomplished by increasing the waste's viscosity (e.g., by dewatering), by mechanical entrapment (i.e., a surface energy phenomenon driven by increased surface area of contact of the viscous fluid bodily wastes with the internal regions of the material or structure) or by any other means known in the art. "Immobilization Under Compressed Inversion," as described further in the Test Method Section below, is measured in terms of the percentage of the viscous fluid bodily waste or analogue that remains in the structure after the structure is subjected to an inverted pressure cycle, as described below. "Retention Under Compressed Inversion", or "retention," is an absolute measure of how much viscous fluid bodily waste remains "stored" under stressful usage conditions.

Preferably, the liquid handling structure should have a Retention Under Compressed Inversion value of greater than about 7.5 g of the viscous fluid bodily waste which penetrates the structure. More preferably, the liquid handling is structure should have a Retention Under Compressed Inversion value of greater than about 8.0 g of viscous fluid bodily waste, and most preferably greater than about 8.5 g of viscous fluid bodily waste after being subjected to the Retention Under Compressed Inversion test, as described below. Generally, Retention Under Compressed Inversion values between at least about 7.5 g and about 100.0 g, and between about 8.0 g and about 100.0 g have been found to be acceptable. Under the same conditions, the liquid handling structure should have an Immobilization Under Compressed Inversion value of at least 70% of the viscous fluid bodily waste accepted by the liquid handling structure. More preferably, the liquid handling structure should have an Immobilization Under Compressed Inversion value of at least about 80% and most preferably at least about 85% of the viscous fluid bodily waste accepted by the element 120. Generally, Immobilization Under Compressed Inversion values between at least about 70% and about 100%, and between about 80% and about 100% have been found to be acceptable. (These preferred Immobilization and Retention Under Compressed Inversion parameters relate to integrated articles which are preferably evaluated as they are intended for use. Accordingly, all of the components or layers of the article should be configured as they would be during normal use when the measurement of their performance is made.)

Without the appropriate immobilization and retention performance, the effects of improved acceptance and storage performance may be diminished because the viscous fluid bodily waste may return to the body-facing surface of the structure, increasing the likelihood of leakage or contamination of the wearer's skin. Further, immobilization is most effective if the structure first accepts the waste and then stores it. Viscous fluid bodily waste that is immobilized prior to being stored away from the wearer's skin may remain on the structured carrier in contact with the skin. Immobilizing viscous fluid bodily waste which is in contact with the skin can increase the effort required by the caregiver during the changing/cleaning process and increases the likelihood of residual, micro-level contamination. "Micro-level contamination" refers to waste residue which remains on the skin, but is not easily visible to the human naked eye. Therefore, it may be helpful to consider at least three parameters (acceptance, storage, and immobilization or acceptance, storage and retention) for a given structure when determining its utility for effectively managing viscous fluid bodily wastes.

In some embodiments, it may be desirable to provide the diaper 20 with different acceptance performance in different portions of the diaper. This may be accomplished by providing a single structured carrier which has been manufactured or treated to have regions of differing acceptance characteristics. Further, the structured carrier may be elevated above the plane of the body-facing surface of the article so as to be in better control of exuded viscous fluid bodily wastes. In some embodiments, it may even be desirable to have the structured carrier in contact with skin of wearer in proximity of the viscous fluid bodily waste source (e.g., the perianal region).

The trans-topsheet capacity as measured by the trans-topsheet capacity test as disclosed hereinafter reflects the diapers ability to handle low-viscosity fecal material. First region 81 and second region 82 of the diaper 20 should have a relatively high trans-topsheet capacity.

There is an inverse relationship between the minimum trans-topsheet capacity necessary to handle low-viscosity fecal material and the surface area of the diaper 20 having this minimum capacity. As a larger percentage of the diaper 20 surface area has a trans-topsheet capacity sufficient to handle low-viscosity fecal material, the necessary trans-topsheet capacity diminishes.

In any case, the first region 81 and the second region 82 of the diaper 20 preferably have a trans-topsheet capacity of at least about 300 grams per square inch provided that an surface area at least 0.02 square meter of the diaper 20 has such a trans-topsheet capacity and preferably at least 0.03 square meter of the diaper 20 has such a trans-topsheet capacity.

At least a portion of the first region 81 and at least a portion the second region 82 of diaper 20 according to the present invention preferably provides a trans-topsheet capacity of at least 300 grams per square meter, more preferably at least 400 grams per square meter, even more preferably at least 500 grams per square meter, still more preferably at least 600 grams per square meter, and most preferably at least 700 grams per square meter.

Liquid Storage Structure

Liquid Storage

The liquid storage structure 28 may be any absorbent means which is generally compressible, conformable, non-irritating to the wearer's skin, and capable of absorbing and retaining liquids such as urine and other certain body exudates. As shown in FIG. 1, the liquid storage structure 28 has a garment surface, a body surface, side edges, and waist edges. The liquid storage structure 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the liquid storage structure 28 may also be varied (e.g., the liquid storage structure 28 may have varying caliper zones, a hydrophilicity gradient, a pore size gradient, a superabsorbent gradient, or lower average density and lower average basis weight acquisition zones; or may comprise one or more layers or structures). The total absorbent capacity of the liquid storage structure 28 should, however, be compatible with the design loading and the intended use of the diaper 20. Further, the size and absorbent capacity of the liquid storage structure 28 may be varied to accommodate wearers ranging from infants through adults.

Exemplary absorbent structures for use as the liquid storage structure 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

Wrap Sheets

The liquid storage structure of the present invention may further comprise at least one wrap sheet. The wrap sheet covers the absorbent structure at least at a part of the surface of the absorbent structure, such that the fluid path from the liquid receiving area to the liquid storage structure will pass through the web. Thus the meaning of the term "wrapping" should not be read to mean complete wrapping or enveloping only. An example for such an embodiment can be a wrap-sheet covering the top surface of the liquid storage structure, and then is being tacked down next to the core, such that the side surface can be but not necessarily have to be covered by the wrap sheet.

In a preferred embodiment, the wrap-sheet covers also other surfaces of the liquid storage structure, in one preferred embodiment, it covers all six surfaces, such that the liquid storage structure is completely enveloped. Another preferred and more easy to manufacture embodiment covers the top surface as well as two side surfaces by being folded around these to partly of fully cover the bottom surface.

The wrapping of the absorbent member can also be achieved by more than more than one wrap-sheet, or by one wrap sheet with different properties in different regions thereof. For example, the surface parts of the absorbent member which are not in the fluid flow path, can have no, or non-permanent fluid hydrophilicity. Or, a different wrap material can be used in such regions, or the absorbent member materials can there be contained by other elements, such as conventional tissue materials, but also impermeable sheets, which may at the same time have another functionality, such as a backsheet material.

Of course, it is an essential requirement, that the absorbent structure and the wrap sheet are in fluid communication with each other, such that the fluid flow path, and particularly the capillary transport gradient will not be interrupted. A preferred embodiment of this is a design, where the wrap sheet and the absorbent structure are in direct contact with each other—at least for the surfaces as described in the above.

It is generally known in the art, to manufacture suitable wrap sheets from tissue layers, nonwovens, and the like. Preferred nonwoven materials to be used for the wrap sheets of the present invention are disclosed for example in European patent application 98107288.7 (Fuchs). These hydrophilic materials exhibit a low surfactant release to the acquired liquid and hence do not negatively impact the liquid handling of the absorbent article of the present invention. In order to not negatively impact the liquid handling of the absorbent article of the present invention, a suitable wrap sheet has a surface tension reduction value of less than 15 mN/m, preferably less than 12 mN/m, more preferably less than 9 mN/, even more preferably less than 6 mN/m, and most preferably of less than 3 mN/m according to the surface tension reduction test defined hereinafter.

Backsheet

The backsheet 26 is positioned adjacent the garment surface of the liquid storage structure 28 and is preferably joined thereto by attachment means (not shown) such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

For example, the backsheet 26 may be secured to the liquid storage structure 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body.

The backsheet 26 prevents the exudates absorbed and contained in the liquid storage structure 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet 26 is a thermoplastic film having a thickness of about 0.012 mm (0.5 mil) to about 0.051 mm (2.0 mils). Particularly preferred materials for the backsheet 26 include RR8220 blown films and RR5475 cast films as manufactured by Tredegar Industries, Inc. of Terre Haute, Id. The backsheet 26 is preferably embossed and/or matte finished to provide a more cloth-like appearance. Further, the backsheet 26 may permit vapors to escape from the liquid storage structure 28 (i.e., be breathable) while still preventing exudates from passing through the backsheet 26.

Structured Carrier

The structured carrier 24 of the present invention has a first or inner surface oriented toward the interior of the disposable diaper, specifically oriented toward the liquid storage structure 28, and an opposed second or outer surface oriented toward the skin of the wearer when the diaper is worn.

The structured carrier 24 is juxtaposed with, but not necessarily adjacent the body surface of the liquid storage structure 28, and is preferably joined to the backsheet 26 or liquid storage structure 28 by means such as those well known in the art. In a preferred embodiment of the present invention, the structured carrier 24 and the backsheet 26 are joined directly to each other in the diaper periphery.

The structured carrier 24 is compliant, soft feeling, and non-irritating to the wearer's skin. Further, the structured carrier 24 is liquid pervious, permitting liquids (e.g., urine) to readily penetrate through its thickness. A suitable structured carrier 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the structured carrier 24 is made of a hydrophobic material to isolate the wearer's skin from liquids contained in the liquid storage structure 28.

General Properties

Functional Properties

The structured carrier of the present invention is hydrophobic and in order to minimize liquid retention in the structured carrier and to minimize liquid rewet from the liquid handling structure or the liquid storage structure back to the skin of the wearer.

Optionally, the structured carrier of the present invention may also be oleophobic in order to minimize liquid retention in the structured carrier and to minimize liquid rewet from the liquid handling structure or the liquid storage structure back to the skin of the wearer.

The structured carrier of the present invention has a liquid retention in the topsheet according to the Liquid-Retention Test defined hereinafter of less than 50 mg, preferably less than 40 mg, more preferably less than 30 mg, most preferably less than 20 mg for a test liquid having a surface tension of about 62 mN/m.

The structured carrier of the present invention has a liquid retention in the topsheet according to the Liquid-Retention Test defined hereinafter of less than 150 mg, preferably less than 120 mg, more preferably less than 90 mg, most preferably less than 70 mg for a test liquid having a surface tension of about 33 mN/m.

The contact angle of the user facing side of the structured carrier of the present invention with distilled water having a surface tension of at least 72 mN/m is at least 90°, preferably at least 100°, more preferably at least 110°, even more preferably at least 120°, most preferably more than 125°. High contact angles reduce the capillary suction of the pores of the structured carrier. Contact angles of more than 90° even result in a negative the capillary suction, hence rendering the respective pores water repellent.

Structural Properties

The structured carrier 24 preferably has a plurality of apertures with an is effective aperture size of at least 0.2 square millimeters, more preferably, the plurality of apertures have an effective aperture size of at least 0.5 square millimeters, even more preferably, the plurality of apertures have an effective aperture size of at least 1.0 square millimeters, even more preferably, the plurality of apertures have an effective aperture size of at least 2.0 square millimeters, and most preferably, the plurality of apertures have an effective aperture size of at least 3.0 square millimeters. Effective apertures are those which have a gray level of 18 or less on a standard gray level scale of 0–255, under the image acquisition parameters described below.

The structured carrier 24 preferably has an effective open area of at least 15 percent, more preferably the structured carrier has an effective open area of at least 20 percent, even more preferably, the structured carrier has an effective open area of at least 25 percent, and most preferably the structured carrier has an effective open area of at least 30 percent.

A method to determine effective aperture size and open area is described in the method section.

Manufacturing Techniques

Suitable materials and structures for use as the structured carrier may include apertured nonwoven webs, apertured films, apertured formed films, scrims, woven webs, scrim, netting, macroporous thin foams, composites of the aforementioned materials, and the like. There are a number of manufacturing techniques which may be used to manufacture the structured carrier 24. For example, the structured carrier 24 may be a nonwoven web of fibers spunbonded, carded, wet-laid, meltblown, hydroentangled, combinations or composite laminates of the above, or the like. Preferred structured carriers 24 include a carded/carded composite, hydroentangled over a wire forming screen and thermally air-through bonded by means well known to those skilled in the nonwovens art and hydroentanglement of fibrous webs.

Surface Treatment

The structured carrier 24 of the present invention may comprise a surface finish reducing the surface free energy of at least a part of the surface of the structured carrier and hence rendering this part of the surface even more hydrophobic and eventually oleophobic.

The structured may comprise hydrophobicity gradients in a direction parallel to the major surfaces of the structured carrier to provide individual liquid handling properties in different regions of the structured carrier. The structured carrier may also comprise a hydrophobicity gradient in a direction perpendicular to the major surfaces of the structured carrier in order to enhance liquid transfer through the structured carrier.

At least a part of the surface, and in particular of the surface facing the wearer during use, of the structured carrier 24 of the present invention may comprise a surface coating such as a thin fluorocarbon polymer film. Suitable techniques to obtain such a surface coating are well known in the art and are described for example in European patent application No. 98116895.8, in WO 97/42356 (Gleason) and in WO96/00548 (Ouellette). Another suitable surface treatment is a silicone release coating from Dow Corning of Midland, Mich. available as Syl-Off 7677 to which a crosslinker available as Syl-Off 7048 is added in proportions by weight of 100 parts to 10 parts, respectively. Another suitable surface treatment is a coating of a UV curable silicone comprising a blend of two silicones commercially available from General Electric Company, Silicone Products Division, of Waterford, N.Y., under the designations UV 9300 and UV 9380C-D1, in proportions by weight of 100 parts to 2.5 parts, respectively. Another suitable treatments include fiber finishs available from Fibervisions of Varde, Denmark, under the designations T190 and T198, a fiber finish available from Schill and Seilacher of Bbblingen, Germany, under the designation Silastol FC1760, a melt-in additive available from the Minnesota Mining And Manufacturing Company, of St. Paul, Minn., USA. Other suitable treatment materials include, but are not limited to, fluorinated materials such as fluoropolymers (e.g., polytetrafluoroethylene (PTFE), commercially available under the trade name TEFLON®) and chlorofluoropolymers. Other materials which may prove suitable for providing regions of reduced surface energy include Petrolatum, latexes, paraffins, and the like.

The structured carrier 24 of the present invention may comprises hydrophobic and oleophobic polymers. Processes to manufacture such polymers and articles therefrom is well known in the art and are described for example in U.S. Pat. No. 3,870,767 (Grimaud).

Optionally, the structured carrier of the present invention may be treated by modulated plasma glow discharge treatments as described in European patent application No. 98116895.8 (D'Agostino et al., P&G case CM1893FQ) and European patent application No. 98116894.1 (D'Agostino, P&G case CM1894FQ).

Skin Care Composition

The outer surface of the structured carrier may comprise an effective amount of a skin care composition which is semi-solid or solid at 20 C. and which is partially transferable to the wearer's skin. In preferred embodiment of the absorbent article of the present invention, the absorbent article additionally comprises an skin care composition which is at least partially transferable to the skin of the user during the intended use. Preferably, such an oil-containing composition is positioned on a user facing surface of the absorbent article. The oil-containing composition may also be deployed in such a way that it is only released at the time of intended use such as being microencapsulated.

Skin care compositions suitable for the absorbent article of the present invention are described for example in WO96/16682 (Roe et al.) incorporated herein by reference.

Liquid Handling Structure

Properties

Positioning

The liquid handling structure is located between the structured carrier and the liquid storage structure. It is preferred that the liquid handling structure be operatively associated with the structured carrier such that fluid bodily waste acquired through the structured carrier may enter the liquid handling structure. In some alternate embodiments, the liquid handling structure may include a leg cuff, the waistband, a fecal waste containment pocket, or the like, or may be operatively associated with any such features.

Preferably, a substantial portion of the liquid handling structure is positioned in the first region of the absorbent article and a portion of the liquid handling structure is positioned in the second region of the absorbent article. In preferred embodiments, at least a part of the liquid handling structure is located in the region of the article that is near the wearer's urethra when worn. At least a part of the liquid handling structure is preferably located in the region of the article that is near the wearer's anal region when worn. This helps ensure that any waste discharged is deposited on or near the liquid handling structure.

Functional Properties

The liquid handling structure of the present invention preferably is capable of accepting, storing, immobilizing and retaining viscous fluid bodily waste that is accepted and stored by the absorbent article. These functions are described above in the context of the entire absorbent article of the present invention.

In addition, the liquid handling structure may transport viscous fluid bodily waste within the absorbent article 20 in directions generally parallel to the plane of the backsheet 26. The transport may be active, such that capillary or other forces result in the movement of the viscous fluid bodily waste or components thereof (e.g., free water). In other embodiments, the transport may be passive whereby viscous fluid bodily waste or components thereof move through the structure under the influence of externally applied forces, such as gravity, wearer pressure or wearer motion. In the case of passive transport, the liquid handling structure should have relatively large, interconnected channels, or the like, such that the viscous fluid bodily waste may readily move through the structure with minimum energy input.

The liquid handling structure of the present invention preferably does not reduce the surface tension of a liquid when the liquid handling structure is in contact with that liquid. Where needed, it is desirable to either use intrinsically hydrophilic materials such as cellulosic fibers, polyester fibers, or the like or to treat the hydrophobic materials with surfactants which are not easily released into the liquid.

Structural Properties

The liquid handling structure of the present invention preferably has a ratio of basis weight to uncompressed caliper of less than 100 grams per square meter per millimeter, i.e. the liquid handling structure has an open structure in order to readily accept body exudates such as urine, menses, faeces, and the like. More preferably, the liquid handling structure of the present invention has a ratio of basis weight to uncompressed caliper of less than 90 grams per square meter per millimeter. Yet more preferably, the liquid handling structure of the present invention has a ratio of basis weight to uncompressed caliper of less than 80 grams per square meter per millimeter. Most preferably, the liquid handling structure of the present invention has a ratio of basis weight to uncompressed caliper of less than 70 grams per square meter per millimeter. Liquid handling structures having a ratio of more than 100 grams per square meter per millimeter may provide a sufficient openness to readily accept high viscosity liquids such as faeces and menses.

The liquid handling structure generally has a basis weight between 5 and 500 grams per square meter. Liquid handling structure having a basis weight of less than 5 g/m² will not be able to provide the desired resiliency and compression resistance. Liquid handling structure having a basis weight of more than 500 g/m² will add unwanted weight to the absorbent article which may cause discomfort by the wearer.

The liquid handling member of the absorbent article of the present invention overcomes the skin marking problems of the prior art liquid handling members by collapsing in those areas where high pressure is exerted onto the liquid handling member by the wearer during use. It has been found that the void volume contained in those areas which are located outside the high-pressure regions is sufficient to acquire and store most loadings with high viscosity liquids. In addition, high viscosity liquids initially stored in a high-pressure region will be automatically moved into a low-pressure region when external pressure is applied to the high-pressure region.

Therefore, the liquid handling member of the present invention is designed to sustain high void volumes under low pressures up to 2758 Pascal (0.4 psi) and is further designed to collapse under high pressures of 3447 Pascal (0.5 psi) and above. Under a confining pressure of 2758 Pascal (0.4 psi), liquid handling member of the present invention has a caliper of at least 70 percent of its caliper under a confining pressure of 689 Pascal (0.1 psi), preferably of at least 75 percent, more preferably of at least 80 percent, even more preferably of. at least 85 percent, most preferably of at least 90 percent. Under a confining pressure of 3447 Pascal (0.5 psi), the liquid handling member of the invention has a caliper of less than 60 percent of its caliper on a confining pressure of 689 Pascal (0.1 psi), preferably of less than 50 percent, more preferably of less than 45 percent, even more preferably of less than 40 percent, most preferably of less than 35 percent.

To provide sufficient void volume in the low-pressure regions, the caliper of the liquid handling member of the present invention under a confining pressure of 689 Pascal (0.1 psi) is at least 0.5 mm, preferably is at least 0.75 mm, more preferably at least 1.0 mm, even more preferably at least 1.25 mm, most preferably at least 1.5 mm. The surface area of the body facing surface of liquid handling member of the present invention preferably is at least 100 square centimeters, more preferably 200 square centimeters, and most preferably 250 square centimeters. The aforementioned values are for babies of about 6 to 9 kilograms may need to be adapted for other sizes.

The term "caliper" of a member as used herein refers to the distance of two planar, parallel surfaces in the z-dimension whereby the two planar surfaces confine the member under a defined confining pressure such as for example 689 Pascals (0.1 psi) and whereby both confining surfaces are perpendicular to the z-dimension of the member. Generally, the z—axis is taken to be perpendicular to the two major surfaces of the member whereby the member is disposed in the absorbent article such that its major surfaces of parallel to the major surfaces of the absorbent article i.e. parallel to the body facing surface and to the garment facing surface of the absorbent article.

"Another key property is the resiliency of the liquid handling structure 29. In order to remain open, the liquid handling structure 29 must have a sufficient resiliency to withstand she forces of packaging and those applied by the wearer. The term "resiliency" as used herein refers to the percentage of recovered caliper after the liquid handling structure has been temporarily compressed under a defined pressure. Preferably, the liquid handling structure 29 has a resiliency of as least 50% after 30 second under an applied pressure of 1 Newton/cm², more preferably, the liquid handling structure 20 has a resiliency of at least 75% after 30 seconds under an applied pressure of 1 Newton/cm², most preferably, the liquid handling structure 29 has a resiliency of at least 85% after 30 seconds under an applied pressure of 1 Newton/cm²."

"In order to not negatively impact the liquid handling of the absorbent article of the present invention, the liquid handling structure has a surface tension reduction value of less than 15 mN/m, preferably less than 12 mN/m, more preferably less than 9 mN/m, even more preferably less than 6 mN/m, and most preferably of less than 3 mN/m according to the surface tension reduction test defined hereinafter."

Structure of the Liquid Handling Structure

The liquid handling structure may be any material or structure capable of accepting, storing, and immobilizing bodily exudates, as described above. Thus, the liquid handling structure may include a single material or a number of materials operatively associated with each other. Further, the liquid handling structure may be integral with another element of the diaper 20 or may be one or more separate elements joined directly or indirectly with one or more elements of the diaper 20. Embodiments are contemplated wherein the liquid handling structure includes at least a portion of the core 28.

Suitable Materials

Suitable materials for use as the liquid handling structure may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, liquid storage structure structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.) The liquid handling structure, or any portion thereof, may include or be coated with a lotion or other known substances to add, enhance or change the performance or other characteristics of the element.

A suitable liquid handling member can be obtained for example by submitting a nonwoven web material (basis weight about 20 grams per m² to about 60 grams per m²) comprising polyester fibers between 3 denier and 9 denier to the process defined in EP patent application 99124637 entitled "Method and apparatus for longitudinally corrugating a web material" filed in the names of Dziezok et al. (P&G case CM2251) or other corrugating processes well known in the art such as creping, ring rolling, and the like. Another suitable liquid handling member may be obtained by using corrugation plates. The above nonwoven web material or another suitable nonwoven web material can be corrugated this way. The corrugation plates can have 6 to 12 loops per inch and a loop height of about 2 to 4 mm. For fixing the corrugated structure of the nonwoven web, the web materials may be kept between the corrugation plates at a suitable temperature of for example about 60° C. for e.g. about 4 hours.

METHODS

"Test methods suitable for measuring the properties described herein are defined in U.S. Pat. No. 6,635,801, this document being incorporated by reference herein."

What is claimed:

1. An disposable absorbent article comprising
   a liquid pervious structured carrier,
   a liquid impervious backsheet at least partially peripherally joined to said structured carrier,
   a liquid storage structure positioned intermediate said structured carrier and said backsheet, and
   a liquid handling structure positioned intermediate said structured carrier and said liquid storage structure, said liquid handling structure having a caliper under a confining pressure of 689 Pascal (0.1 psi) of at least 0.5 mm, and having a resiliency of at least 50% after 30 seconds under an applied pressure of 1 Newton/cm$^2$,
   wherein said liquid handling structure has a caliper under a confining pressure of 2756 Pascal (0.4 psi) of at least 80% of said liquid handling structure's caliper under a confining pressure of 689 Pascal and said liquid handling structure has a caliper response to a change in confining pressure from 689 Pascal to 2456 Pascal that is less than a caliper response to a change in confining pressure from 2456 Pascal to 3447 Pascal (0.5 psi) whereby said liquid handling structure has a caliper of at a confining pressure of 3447 Pascal that is less than 60% of said liquid handling structure's caliper under a confining pressure of 689 Pascal.

2. A disposable absorbent article according to claim 1 said disposable absorbent article having a transverse centerline, a first region forward of said transverse centerline being positioned adjacent to the front waist region of the wearer during use, and a second region backward of said transverse centerline being positioned adjacent to the back waist region of the wearer during use wherein at least a substantial part of said liquid handling structure is positioned in said first region.

3. A disposable absorbent article according claim 1 said disposable absorbent article having a transverse centerline, a first region forward of said transverse centerline being positioned adjacent to the front waist region of the wearer during use, and a second region backward of said transverse centerline being positioned adjacent to the back waist region of the wearer during use wherein at least a substantial part of said liquid handling structure is positioned in said second region.

4. A disposable absorbent article according to claim 1 wherein said structured carrier comprises an apertured nonwoven web material having a plurality of apertures, said apertures having a surface area of at least 0.2 mm$^2$.

5. A disposable absorbent article according to claim 1 wherein said disposable absorbent article has a front region skin hydration value of less than 100 mg.

6. A disposable absorbent article according to claim 1 wherein said disposable absorbent article has a storage under pressure capacity of at least 800 g/cm$^2$.

* * * * *

UNITED STATES PATENT AND TRADEMARK OFFICE
CERTIFICATE OF CORRECTION

PATENT NO. : 6,786,894 B2
DATED : September 7, 2004
INVENTOR(S) : Michael Divo et al.

It is certified that error appears in the above-identified patent and that said Letters Patent is hereby corrected as shown below:

Column 2,
Line 31, delete "coordinated" and insert -- co-ordinated --.
Line 45, delete "flat-out," and insert -- flatout, --.

Column 6,
Line 60, delete "body-facing" and insert -- bodyfacing --.

Column 8,
Line 54, delete "9 mN/," and insert -- 9 mN/m, --.

Column 13,
Line 44, delete "of. at least 85 percent," and insert -- of at least 85 percent, --.

Column 14,
Line 12, delete "withstand she forces" and insert -- withstand the forces --.
Line 17, delete "of as least" and insert -- of at least --.

Signed and Sealed this

Twenty-eighth Day of February, 2006

JON W. DUDAS
*Director of the United States Patent and Trademark Office*